(12) United States Patent
Gessler et al.

(10) Patent No.: US 8,785,642 B2
(45) Date of Patent: Jul. 22, 2014

(54) PROCESS FOR PREPARING 6-SUBSTITUTED-1-(2H)-ISOQUINOLINONES AND INTERMEDIATE COMPOUND

(75) Inventors: Simon Gessler, Mannheim (DE); Theo Wollmann, Hattersheim (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/534,698

(22) Filed: Jun. 27, 2012

(65) Prior Publication Data

US 2013/0012711 A1    Jan. 10, 2013

(30) Foreign Application Priority Data

Jul. 8, 2011    (EP) .................................. 11305892.9

(51) Int. Cl.
*A61K 31/47*    (2006.01)
*C07D 217/22*    (2006.01)

(52) U.S. Cl.
USPC .......................................... 546/141; 514/309

(58) Field of Classification Search
CPC .............................. A61K 31/47; C07D 217/22
See application file for complete search history.

(56) References Cited

U.S. PATENT DOCUMENTS 3,732,245 A * 5/1973 Batcho et al. ................ 548/508

FOREIGN PATENT DOCUMENTS

WO    WO 2009/080335 A1 *  7/2009
WO    WO2009/080335 A1    7/2009

OTHER PUBLICATIONS

Ohkubo, M. et al. Practical Synthesis of Indolopyrrolocarbazoles. Tetrahedron. 1996, vol. 52, p. 8101, scheme 1.*

Gordon, MS. et al. Substituted Silabenzenes. Organometallics. 1998, vol. 7, p. 146, table II.*
Repke, David B., "Psilocin Analogs. III. Synthesis of 5-Methoxy- and 5-Hydroxy-1,2,3,4-tetrahydro-9H-pyrido[3,4-b] indoles," Journal of Heterocyclic Chemistry (1982), vol. 19, pp. 845-848.
Leonardi, A. et al., "Synthesis and pharmacological evaluation of new indole derivatives structurally related to thymoxamine," European Journal of Medicinal Chemistry (1994), vol. 29, pp. 551-559.
Ohkubo, Mitsuru et al., "Practical Synthesis of Indolopyrrolocarbazoles," Tetrahedron (1996), vol. 52, No. 24, pp. 8099-8112.
Boini, Sathish et al., "Development of a Manufacturing Process for 1-(1-Pyridin-2-yl methyl-piperidin-4-yl)-1-H-indole: A Key Intermediate for Protein Kinase C Inhibitor LY317615," Organic Process Research & Development (2006), vol. 10, pp. 1205-1211.
European Search Report dated Oct. 4, 2011 issued in EP11305892.
International Search Report dated Aug. 7, 2012 issued in PCT/EP2012/062202.

* cited by examiner

*Primary Examiner* — Rita Desai
*Assistant Examiner* — Ben S Michelson
(74) *Attorney, Agent, or Firm* — Scully, Scott, Murphy & Presser, P.C.

(57) ABSTRACT

The present invention relates to novel substituted phenyl compounds of the formula (VI)

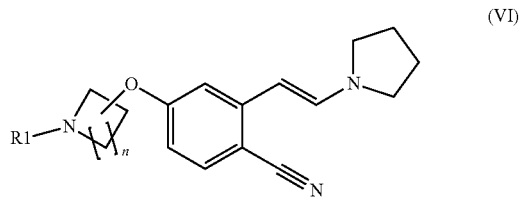

and to a process for making them. The compounds can be used as intermediates for making 6-substituted-1-(2H)-isoquinolinone derivatives.

16 Claims, No Drawings

PROCESS FOR PREPARING 6-SUBSTITUTED-1-(2H)-ISOQUINOLINONES AND INTERMEDIATE COMPOUND

The present invention relates to a compound of the formula

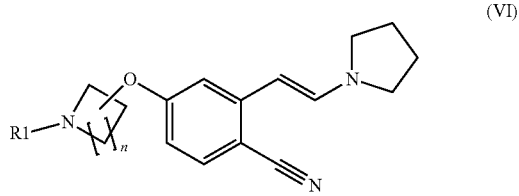

(VI)

wherein
n is 1, 2, 3 or 4 and R1 is H or a protecting group. The present invention further relates to a new process for preparing such a compound. It also relates to the use of such a compound as intermediate in the preparation of a 6-substituted-1-(2H)-isoquinolinone derivative of formula (I)

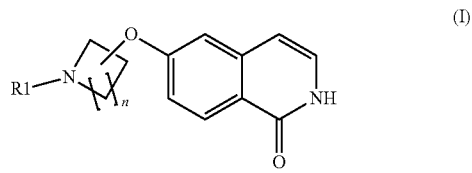

(I)

The compounds of formula (I) are inhibitors of the enzyme Rho-Kinase or can be used as intermediates in the preparation of further inhibitors of the Rho-Kinase enzyme, which are beneficial for the treatment of inter alia, hypertension. Such derivatives are described e.g. in WO 2007/012421, WO 2007/065916 and WO 2008/077550.

A further synthetic route for the preparation of a compound of formula (I) is described in WO 2009/080335. The route described makes use of alkoxy-bis(dialkylamino) methane derivatives as reagent in the preparation of a different intermediate, especially by using tert-Butyloxy-bis-(dimethylamino)methane. However, these reagents are expensive especially if for use at large scale and in the case of tert-Butyloxy-bis-(dimethylamino)methane the reagent is not well characterised.

Accordingly, it is the object of the present invention to provide an alternative route for the preparation of compound (I) which is easier and cheaper to perform especially on large scale and which preferably yields the product in a higher yield. The problem has been solved by the present invention and a new synthetic route is provided, which allows the preparation of a compound of formula (I) in a few chemical reaction steps under the described reaction conditions in high yield with readily available starting materials and reagents. These derivatives may be used itself as Rho-kinase inhibitors or may be used as an intermediate in the synthesis of further inhibitors by modifying the amino group in these compounds by adding further substituents to the N-atom or by modifying any other position in the isoquinolinone system.

DEFINITIONS

The term alkyl and the corresponding alkylene substituents as used are understood as a hydrocarbon residue which can be linear, i.e. straight-chain, or branched and has 1, 2, 3, 4, 5 or 6 carbon atoms, respectively, as indicated in e.g. $(C_1-C_6)$alkyl or $(C_1-C_4)$alkyl or $(C_1-C_2)$alkyl. This also applies if an alkyl group occurs as a substituent on another group, for example in an alkoxy group (O-alkyl) or an alkoxycarbonyl group or an arylalkyl group. Examples of alkyl groups are methyl, ethyl, propyl, butyl, pentyl (amyl) or hexyl, the n-isomers of all these groups, or the branched isomers isopropyl, isobutyl, 1-methylbutyl, isopentyl, neopentyl, 2,2-dimethylbutyl, 2-methylpentyl, 3-methylpentyl, isohexyl, sec-butyl, tert-butyl (1,1-dimethylethyl) or tert-pentyl (1,1-dimethylpropyl, tert-amyl). Corresponding alkylene groups are methylene, ethylene, propylene and the like.

Halogen means fluoro (F), chloro (Cl), bromo (Br) or iodo (I).

Aryl means phenyl or naphtyl, preferably phenyl, unsubstituted or substituted with one, two or three, preferably one, substituents independently selected from $(C_1-C_4)$alkyl, $O(C_1-C_4)$alkyl or halogen. In an alkylenearyl group, such as —$(C_1-C_4)$alkylenearyl or methylenenaryl, the alkylene may be substituted one, two or three times by an aryl on the same or different carbon atoms. Alkylenearyl includes e.g. phenylmethylene (also designated benzyl), (triphenyl)methylene (also designated trityl), (diphenyl)methylene (also designated benzhydryl) or (4-methoxyphenyl)-diphenylmethylene.

DETAILED DESCRIPTION

The overall process steps to make the new compounds and to use them as intermediates in the preparation of a compound of formula (I) are shown in scheme 1. In this regard compound (VI) and the reaction step (B) and also step (C) in the following scheme are embodiments of the present invention.

Scheme 1

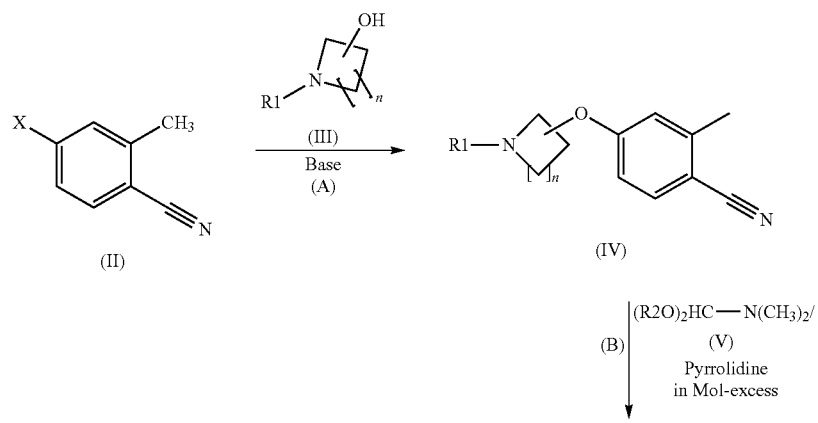

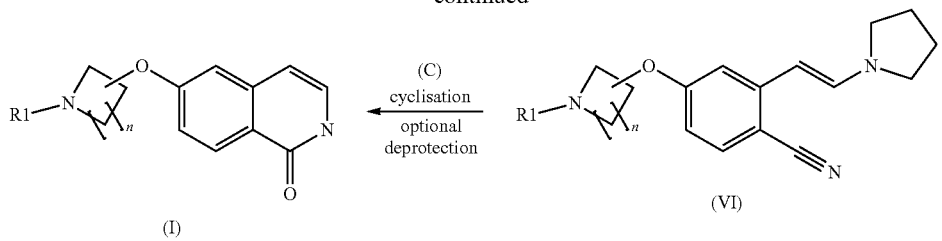

The process steps are described in more detail below.
Preparation of Compound (VI)

In one embodiment the present invention relates to a process for the preparation of a compound of formula (VI)

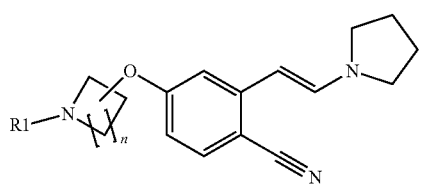

wherein
n is 1, 2, 3 or 4 and
R1 is a H or a protecting group;
comprising
(B) reacting a compound of formula (IV)

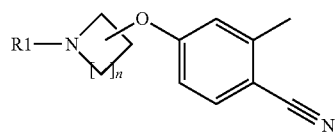

wherein
R1 is a protecting group and
n is 1, 2, 3 or 4;
with a reagent of the formula $(R2O)_2HC-N(CH_3)_2$ (V) wherein R2 is $(C_1-C_6)$alkyl, and pyrrolidine,
wherein reagent (V) is used in a molar excess of 1.5 or more equivalents and pyrrolidine is used in a molar excess of 4.0 or more equivalents over a compound of formula (IV); and
optionally removing the protection group in a compound of formula (VI) to give a compound of formula (VI) wherein R1 is H.

In one embodiment of the process R1 is H. In another embodiment R1 is a protecting group.

The formylation of 2-methyl-nitrobenzene and derivatives thereof with dimethyl formamide acetals is the known starting point for the so called Leimgruber-Batcho indole synthesis (Leimgruber, W.; Batcho, A. D. U.S. Pat. No. 3,732,245), where a strongly electron-withdrawing nitro group serves to acidify the methyl group in the ortho position. Mild formylation with N,N-dimethylformamide dimethylacetal (DMFDMA, $(CH_3O)_2CH-N(CH_3)_2$) converts the methyl group to a beta-dimethylamino-styrene, which collapses to the indole on reduction of the nitro group to the amine (Scheme 2).

Scheme 2

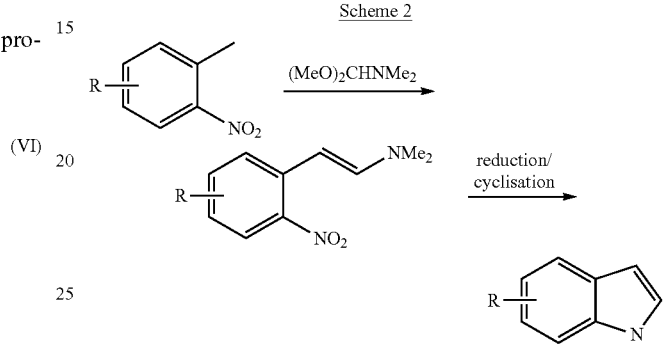

In WO 2009/080335 (Scheme 2) a phenyl compound having a CN group instead of a nitro group has been tried to react. It is stated on page 13 that the use of dimethylformamide dialkoxyacetals according to U.S. Pat. No. 3,732,245 were met with failure. Corresponding negative results obtained by reacting a compound of formula (IVa) according to Scheme 3, wherein R1 is tert-butyloxycarbonyl and n is 3, with different DMF-dialkoxyacetals are shown in Table 1 below.

Scheme 3

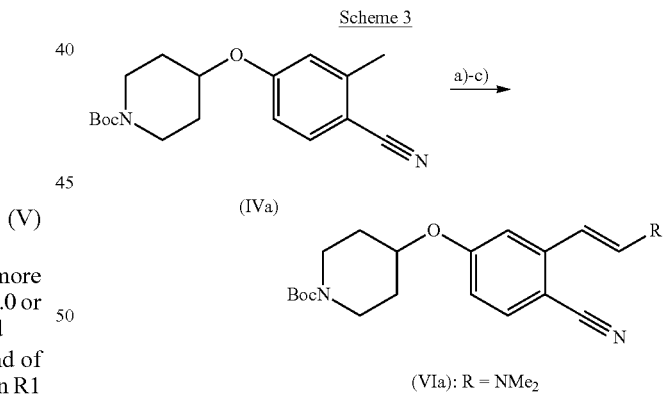

TABLE 1

| Entry | Conditions | Product |
|---|---|---|
| a) | DMF-diisopropylacetal, DMF, 130° C., Pyridine, Triethylamine | starting material (IVa) |
| b) | DMF-dimethylacetal, DMF, 130° C., DABCO, DBU, NaH | starting material (IVa) |
| c) | DMF-dimethylacetal, 130° C. | starting material (IVa) |

This reaction has also been reported by others to take place if pyrrolidine or piperidine is added to the reaction mixture. However, no substituent other than a nitro group ortho to the methyl group has yet been reported to be useful and possible in this reaction. The nitro group is constantly used since it is known to highly activate the methyl group. In the literature the reaction has been described by using usually about stoichiometric amounts (1-1.5 equivalents) of DMFDMA and of pyrrolidine such as e.g. described by a) Repke in J. Heterocycic Chem. (1992, 19, 845-848) where the ratio of nitro-compound (40)/DMFDMA/pyrrolidine is 20.6/22.7/24.0 mmol;

b) Boini in Organic Process Research & Development (2006, 10, 1205-1211) wherein the ratio of 2-nitrotoluene/DMFDMA/pyrrolidine is 2.19/2.63/2.63 mol;

c) Leonardi in Eur. J. Med. Chem. (1994, 29, 551-559) wherein the ratio of nitro compound 17/DMFDMA/pyrrolidine is 0.077/0.115/0.115 mmol with up to 3 equivalents as e.g. used by Ohkubo in Tetrahedron (1996, 52, 24, 8099-8112) wherein the ratio of nitro compound 12a/DMFDMA/pyrrolidine is 3.09/9.27/9.27 mol (773 ml).

Moreover, as mentioned above, there is nothing in the prior art which would lead a skilled person to increase the amount of the acetal reagent (V) and/or to use a certain amount of pyrrolidine in order to achieve a conversion of the much less reactive CN substituted phenyl substrate.

Indeed, if pyrrolidine was added in the amounts usually described in the literature such as 0.1-3.0 mol-equivalents in relation to a compound (IVa), the reaction to obtain compound (VIb) did not work or gave (VIb) in low yield only (Scheme 4; Table 2-entries a), b) and c)).

Scheme 4

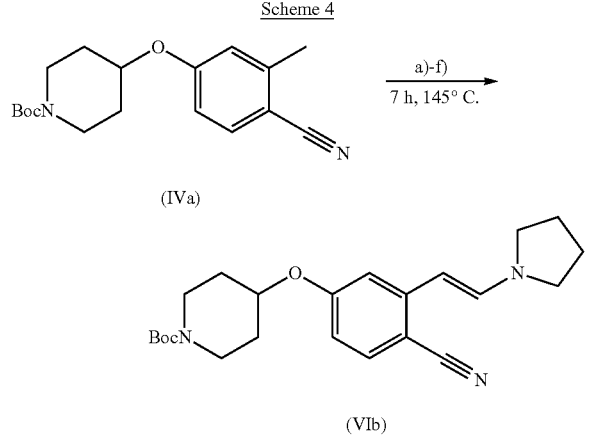

(IVa)

a)-f)
7 h, 145° C.

(VIb)

TABLE 2

| Entry | Conditions | Conversion into (VIb) |
|---|---|---|
| a) | DMFDMA (1 equiv.)/<br>Pyrrolidine (1 equiv.) | 9% |
| b) | DMFDMA (2.2 equiv.)/<br>Pyrrolidine (1 equiv.) | 7% |
| c) | DMFDMA (6 equiv.)/<br>Pyrrolidine (0.1 equiv.) | 0% |

Accordingly, there is an expectation that the reaction will not work with reagent (V) on such a substrate. However, in contrast to this expectation it has been found that the reaction is actually possible to perform under the conditions specified herein and to obtain a product with a high yield and high purity (see Scheme 4; Table 3-entries d), e) and f)).

TABLE 3

| Entry | Conditions | Conversion into (VIb) |
|---|---|---|
| d) | DMFDMA (2 equiv.)/<br>Pyrrolidine (6 equiv.) | 90% |
| e) | DMFDMA (6 equiv.)/<br>Pyrrolidine (6 equiv.) | 100% |
| f) | DMFDMA (3 equiv.)/<br>Pyrrolidine (6 equiv.) | 100% |

The overall reaction of this step is shown in Scheme 5 wherein a compound of formula (IV) with n being 3 is shown by way of example.

Scheme 5

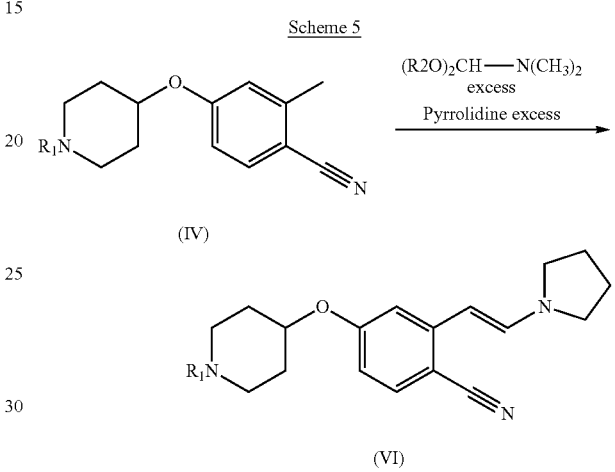

(IV)

$(R2O)_2CH-N(CH_3)_2$
excess
Pyrrolidine excess
→

(VI)

In one embodiment R2 is $(C_1-C_4)$alkyl. In another embodiment R2 is methyl and the reagent $(R2O)_2CH-N(CH_3)_2$ is N,N Dimethylformamid-dimethylacetal (DMFDMA). In a further embodiment of reagent (V) R2 is n-butyl and the reagent is N,N Dimethylformamid-dibutylacetal. Other suitable formamide acetales are N,N Dimethylformamid-diethylacetal, N,N Dimethylformamid-dipropylacetal or N,N Dimethylformamid-diisopropylacetal.

The relative amounts of reagent (V) and of pyrrolidine used in relation to compound (IV) are part of the present invention. Although there is a minimum in the reagents there is in principle no maximum in the excess of reagent (V) or pyrrolidine for performing the reaction. However, for practical reasons the amount of reagent (V) and pyrrolidine used is not higher than necessary for performing the reaction.

Therefore, in one embodiment of the invention the amount of reagent (V), such as DMFDMA, relative to compound (IV) is in the range of 2.0 to 7.0 mol-equivalents. In another embodiment the range is 2.0-4.0 mol-equivalents. In a further embodiment it is 2.0-3.0 mol-equivalents. In yet another embodiment the amount of DMFDMA is 2.2 mol-equivalents.

In one embodiment the ratio of pyrrolidine is in the range of 4.0 to 9.0 mol-equivalents relative to compound (IV). In another embodiment pyrrolidine is used in the range of 4.0 to 7.0 mol-equivalents. In yet another embodiment the pyrrolidine is used in a range of 5.0 to 7.0 mol-equivalents relative to compound (IV). In a further embodiment pyrrolidine is used in about 6.6 mol-equivalents. With the use of this reagent mixture a substantially complete conversion of the compound of formula (IV) to (VI) is obtained.

No other compound than pyrrolidine has shown to be useful in this reaction. Similar compounds like piperidine, morpholine, dimethylamine or a tertiary amine, such as trimethylamine, described in the art, (see review article Heterocycles, 22, 1, (1984), p 195-221, especially page 198-200, and references cited therein) for that purpose had no effect.

In a further embodiment of step B) according to the present invention DMF (dimethylformamide) may optionally be added to the reaction mixture. It has been found that adding a certain amount of DMF to the reaction mixture further catalyses the reaction and further improves the yield of compound (VI). There is no limit in the amount of DMF added. However, for practical purposes the amount in which DMF may be added is limited and is not more than necessary. In one embodiment the amount can vary from about 0.1-4.0 mol-equivalents, preferably about 2.0-3.0 mol-equivalents, relative to compound (IV). A further increase of DMF does not increase the overall yield. A further advantage of using DMF is that the amount of pyrrolidine can be reduced and is in the range of 4.0 to 6.0 mol-equivalents. With the use of DMF the reaction time and/or the temperature for the reaction can be reduced thereby resulting in a higher yield and much cleaner product. Without DMF the yield of a compound of formula (VI) is about 70-85% (Example 2a) whereas with DMF the yield is above 90% after work-up (Examples 2b, 2c).

A significant improvement in the yield has been obtained in the present invention for intermediate (VI) compared with the overall yield of the intermediates obtained in the reactions described in the art. The present invention also provides a more economical synthesis for the new intermediate (VI) by way of using readily available reagents.

A compound of formula (IV) may be added directly without prior dilution in a solvent to the mixture of reagent (V) and pyrrolidine and optionally DMF. Alternatively a compound of formula (IV) may be dissolved in a suitable solvent such as DMF in an appropriate amount as specified above and reagent (V) and pyrrolidine are added subsequently. In another alternative, a lower boiling ether, such as MTBE (methyl-tert-butylether), can be used as solvent. Advantageously, this solvent is continuously removed by distillation to a large extend before reagent (V) and pyrrolidine and optionally DMF are added. The mixture is heated whereby remaining ether but also the products originating from the reaction of compound (V), such as methanol or butanol and dimethylamine are removed.

The temperature used for performing the reaction is in a range of 80°-200° C., preferably 90°-180° C., more preferably 120-170° C. With the addition of DMF the temperature can be lower with a suitable temperature range being about 100° C.-120° C. The time used for reaction is one sufficient to obtain conversion from compound (IV) into compound (VI) and is, for example, from 2 to 27 hours. With the addition of DMF the reaction time can be shorter and a suitable range is from 2 to 10 hours.

The product obtained can be isolated and further purified by standard synthetic techniques. For example, isolation may be done by evaporation of the reaction mixture followed by a regular aqueous work-up and a subsequent crystallisation of the product. Alternatively, the product contained in the reaction mixture may also be precipitated directly from the reaction mixture by adding a suitable anti-solvent such as water and/or alcohols.

The acetals of DMF of the general formula $(R2O)_2CH-N(CH_3)_2$ (V), including DMFDMA, may be prepared as described by Brederck in Chemische Berichte 1968, 101, 41-50 or can be obtained commercially from various suppliers.

While the stereochemistry of the enamine in (VI) is drawn as E-isomer, it may exist as both E and Z isomer, which are synthetically equivalent.

A protecting group R1 can be chosen from a group as outlined under "Protecting group" below.

Preparation of Compound (I)

In a further embodiment the present invention relates to a process for the preparation of a compound of formula (I)

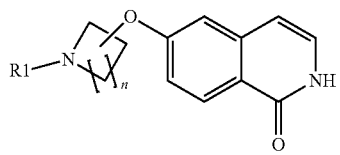

(I)

or a salt thereof, wherein
n is 1, 2, 3 or 4; and
R1 is H or a protecting group,
comprising the steps of
(B) preparing a compound of formula (VI) as shown in Scheme 1

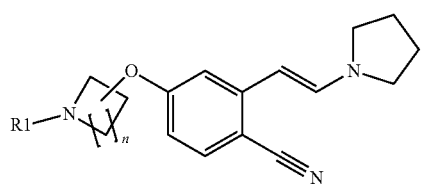

(VI)

wherein
n is 1, 2, 3 or 4; and
R1 is a protecting group;
according to the process as described above, and
(C) cyclising a compound of formula (VI) in a suitable solvent and in the presence of a hydrohalic acid and whereby the protecting group is optionally removed to give a compound of formula (I)

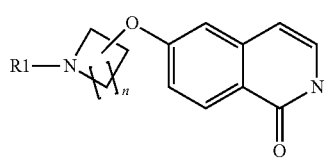

(I)

wherein R1 is H or a protecting group;
(D) optionally the protecting group is removed from a compound of formula (I) obtained in step (C), wherein R1 is a protecting group, to give compound a formula (I) wherein R1 is H, and
(E) optionally, a compound of formula (I) is converted into a salt thereof.

The transformation of 4-heterocycloalkoxy-2-(2'-pyrrolidinyl-vinyl)benzonitriles of formula (VI) to 6-heterocycloalkoxy-1-(2H)-isoquinolinones of formula (I) is not described in the literature. What has been described in WO 2009/080335 is the cyclisation of the dimethylamino derivative. Conditions and cyclisation reagents were found that furnished the desired 6-heterocycloalkoxy-1-(2H)-isoquinolinone (I). These cyclisation conditions and reagents used herein are part of the present invention. In an embodiment, the cyclisation reaction of 4-heterocycloalkoxy-2-(2'-pyrrolidinyl-vinyl)benzonitriles of formula (VI) to a compound of formula (I) can be performed by reacting a compound of formula (VI) in the presence of a strong acid as cyclising reagent, i.e. to perform the reaction under acidic reaction conditions. Under acidic conditions it is understood to perform the cyclisation reaction in the presence of a hydrohalic acid such as HCl, HBr or HI, preferably HCl, in a suitable solvent such as an alcohol, especially using a ($C_1$-$C_6$)-alkanol as solvent such as methanol, ethanol, propanol, butanol or pentanol. Both the n-alcohols as well as the isomers can be used. Preferably, the reaction is performed in methanol, ethanol, n-propanol or n-butanol, with n-butanol being most preferred.

As a source for a hydrohalic acid gaseous HCl or HBr or HI may be used and added to the alcohol. As an alternative to the use of gaseous HCl, other reagents, such as TMSCl or AcCl (acetylchloride), which react with an alcohol to form an anhydrous alcoholic HCl solution, can also be used. A preferred set of reaction conditions for cyclisation involves the use of gaseous HCl in a ($C_1$-$C_6$)-alkanol, such as n-butanol, as solvent.

The reaction is performed in a temperature range of 40° C. to 140° C., more preferred the temperature range is 60° C. to 120° C., depending on the boiling point of the alcohol used.

The reaction is performed using 2 to 30 Mol-equivalents of the hydrohalic acid, such as gaseous HCl, more preferably by using 3 to 15 Mol-equivalents. On a technical scale, the excess of the hydrohalic acid such as HCl can be easily neutralized in a basic scrubber.

In the cyclisation reaction the protecting group may optionally also be removed simultaneously to obtain a compound of formula (I) wherein R1 is H. On the choice of the protecting group in R1 to obtain a compound of formula (I) wherein R1 is H or a protecting group see the paragraphs on "Protection group".

Preparation of Compound (IV)

The compound of formula (IV) used in connection with the process of the present invention to make a compound of formula (VI) can be prepared by a nucleophilic aromatic substitution. The reaction for preparing a compound of formula (IV) is described in WO 2009/080335.

The compound of formula (IV) is prepared by
(A) reacting a compound of formula (II)

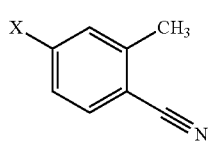
(II)

wherein X is halogen,
in a suitable solvent and in the presence of a base selected from an alkali metal alkoxide, alkali metal hydride or alkali metal with a compound of formula (III)

(III)

wherein
R1 is H or a protecting group and
n is 1, 2, 3 or 4
to give a compound of formula (IV)

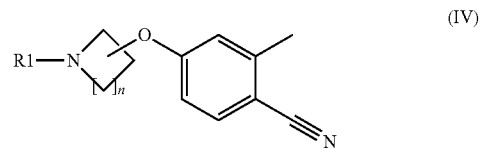
(IV)

and, if R1 is H, the amino group in a compound of formula (IV) is protected to give a compound of formula (IV), wherein R1 is a protecting group.

In one embodiment compound (III) is protected before it is reacted with compound (II). A suitable protected alcohol of formula (III) is 1-Benzyl-3-pyrrolidinol, 3-Hydroxy-piperidine-1-carboxylic acid tert-butyl ester, 1-Benzhydryl-azetidin-3-ol or 4-Hydroxy-piperidine-1-carboxylic acid tert-butyl ester.

Conditions according to which compound (IV) can be prepared are as follows.

Scheme 6

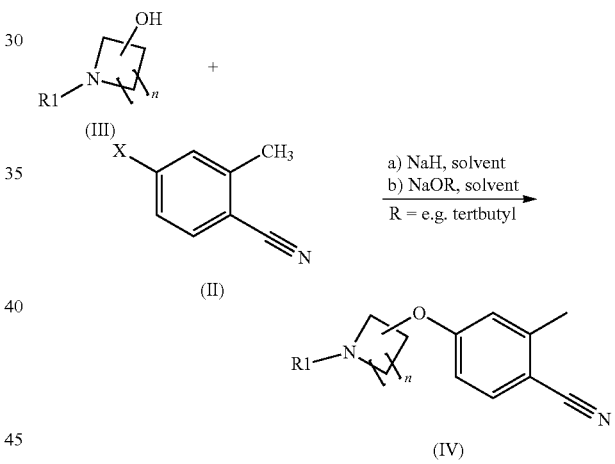

In one embodiment the base is selected from sodium or potassium tert-butoxide (KOtBu), sodium or potassium tert-amylate. In another embodiment the base is NaH. In a more preferred embodiment potassium tert-butoxide or potassium-tert-amylate are used as bases, most preferred potassium tert-butoxide is used.

Solvents which can be used in this reaction step, including variants a) and b) described in Scheme 6 above, are ethers such as Tetrahydrofuran (THF), 2-Methyl-THF, Methyl-tertbutyl ether (MTBE), Dioxane, Dimethoxyethane (DME) or Dimethoxymethane as well as dipolar aprotic solvents like Dimethylsulfoxide (DMSO), N-Methyl pyrrolidone (NMP), N-Ethyl pyrrolidone, Dimethylformamide (DMF) or Dimethylacetamide. In an embodiment a base/solvent mixture is potassium tert-butoxide with MTBE.

The temperature used is usually in the range of 4° C. to 220° C., preferably in the range of 80° C. to 200° C. and more preferably in the range of 40° C. to 140° C. When using lower boiling solvents, it is possible to perform the reaction under pressure in an autoclave. The reaction time is not critical and may vary depending on the solvent and temperature used. The reaction is performed until most or all of the precursors (II) and (III) have reacted, which is usually takes place within several hours and is usually completed within 12 hours.

The preparation of a compound of formula (IV) is also an object of the present invention if thereafter compound (IV) is converted into a compound (VI) according to the process of the present invention.

Protecting Group

The protecting group useful in one of the above mentioned reaction steps A), B) and C) and in the corresponding intermediates can be selected from a variety of groups e.g. listed in but not limited to those mentioned in: T. W. Greene and P. G. M. Wuts: Protective Groups in Organic Synthesis, Third Edition, John Wiley and Sons, New York, 1999 Chapter 7, page 494. Moreover, reference is made to WO2009/080335 where suitable groups in connection with the synthesis of compounds of formula (IV) and (VI) and (I) have been described.

The protecting group in R1 is preferably one which is stable under the basic reaction conditions used in step A) and B). Suitable stable protecting groups R1 useful in step A) and also steps B) and C) and in the intermediates (III), (IV) and (VI) can be selected from carbamates such as tert-butyloxycarbonyl and benzyloxycarbonyl or p-methoxybenzylcarbonyl, amides such as formyl or acetyl, N-alkylenearyls such as benzyl, (diphenyl)methylene, trityl or (4-methoxyphenyl)diphenylmethylene or N—P and N-sulfonyl protecting groups such as dialkyl phosphoramidates and p-toluenesulfonyl.

The protecting group can be introduced by methods known in the art whereby a N-heterocycloalkylalcohol of formula (III), wherein R1 is H, is reacted with a corresponding protecting group providing reagent to deliver the protected amine. In another embodiment, the protecting group may be introduced in a compound of formula (IV), if R1 is H, obtained in a reaction outlined above. Suitable reagents to be used for introducing the protecting group are know in the art and are commercially available. For example, Di-tert-butyl-dicarbonat may be used for introducing the tert-butyloxycarbonyl group.

Preferably the same protecting group is used throughout the synthesis. Accordingly a protecting group stable under basic reaction conditions is preferably used in steps A) and B) and C). Most suitable are base stable but acid labile protecting groups, which can be simultaneously cleaved of in the same reaction step where the cyclisation reaction takes place and a compound of formula (I) is obtained in step C) wherein R1 is H.

In an embodiment of the present invention an acid labile protecting group is used as a protecting group for R1 in a compound of formula (III), (IV) and (VI). In one embodiment of such an acid labile group tert-butyloxycarbonyl is used for R1, which is also stable under the basic reactions for making compound (IV). With the acid labile group the cyclisation reaction of a compound of formula (VI) with a hydrohalic acid gives directly a compound of formula (I) wherein R1 is H. With the use of an acid labile group a separate deprotection step (D) can be omitted.

Where it is desirable that the protecting group is removed after the reaction step (C), the removal of the protecting group may be done in a separate step (D) with prior isolation of the intermediate containing the protecting group or the reaction mixture obtained after the cyclisation reaction may directly be used in the deprotection step.

In an embodiment a compound of formula (I) is prepared by the process of the present invention wherein R1 is H. In another embodiment a compound of formula (I), wherein R1 is H, is directly prepared in step (C) by removing the protecting group.

A compound of formula (I), wherein R1 is H or a protecting group, preferably H, is optionally converted into a salt thereof. Compound (I) can be directly obtained as a salt if the acid is not removed from the cyclisation step in order to obtain the free base. The acid used in the cyclisation step may also be removed and exchanged against another acid by known methods to prepare the corresponding salt of a compound of formula (I).

Salts of a compound of formula (I), incl. pharmaceutically acceptable salts, may be prepared from inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, lactic, maleic, malic, methanesulfonic, succinic, p-toluenesulfonic and tartaric acid by methods known in the art.

In another embodiment of the present invention a compound of formula (I), wherein R1 is H, prepared by the process of the present invention may be used as an intermediate in the synthesis of further derivatives thereof having R1 substituents other than H for making Rho-kinase inhibitors. The present invention relates to a process of making a compound of formula (I) wherein R1 is H and, in a second step, a compound of formula (I') is prepared, wherein R1 becomes R7, by reacting a suitable chemical equivalent of a R7 group with a compound of formula (I). For example a suitable aldehyde R7-C(O)H, wherein R7 is e.g. (C$_1$-C$_6$)alkyl or a further substituted (C1-C6)alkyl group, may be reacted via reductive amination procedure as described in WO 2007/012421 with a compound of formula (I) wherein R1 is H to obtain a (C$_1$-C$_6$)alkyl substituted 6-heterocycloalkoxy-1-(2H)-isoquinolinone (I').

In another embodiment the present invention relates to a process for the preparation of a compound of formula (I)

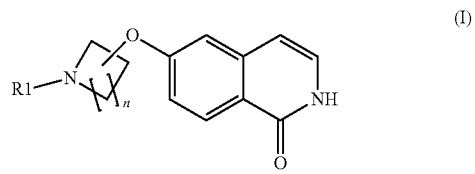

or a salt thereof,
wherein
n is 1, 2, 3 or 4 and R1 is H or a protecting group,
comprising the steps of
(C) cyclising a compound of formula (VI)

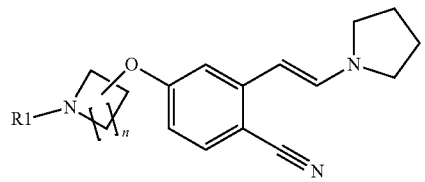

wherein R1 is a protecting group and
n is 1, 2, 3 or 4;
in a suitable solvent and in the presence of a hydrohalic acid and thereby optionally removing the protecting group to give a compound of formula (I)

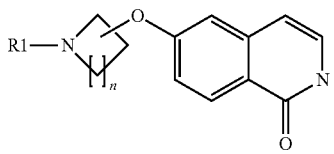

(I)

wherein R1 is H or a protecting group;
(D) optionally removing the protecting group from a compound of formula (I), if R1 is a protecting group, to give compound a formula (I) wherein R1 is H, and
(E) optionally converting a compound of formula (I) into a salt thereof.

This process corresponds to the cyclisation step (C) in the above described synthesis of a compound of formula (I). Accordingly the statements and embodiments mentioned above in connection with step (C), (D) and (E) also apply to this process embodiment here.

In another embodiment the present invention relates to a compound of formula (VI)

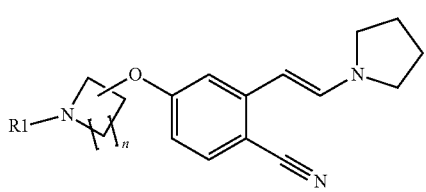

(VI)

wherein R1 is H or a protecting group and n is 1, 2, 3 or 4.

In one embodiment, R1 is a protecting group. In another embodiment R1 is H.

In one embodiment of a compound of formula (VI) R1 is a protecting group having the features mentioned above for the protecting group, including being an acid-labile protecting group, preferably selected from a carbamate, such as the tert-butyloxycarbonyl group, benzyloxycarbonyl group or p-methoxybenzylcarbonyl.

In one embodiment, the protecting group is tert-butyloxycarbonyl and thus in a further embodiment the compound of formula (VI) is 4-[4-Cyano-3-((E)-2-pyrrolidin-1-yl-vinyl)-phenoxy]-piperidine-1-carboxylic acid tert-butyl ester (VIb), having the formula

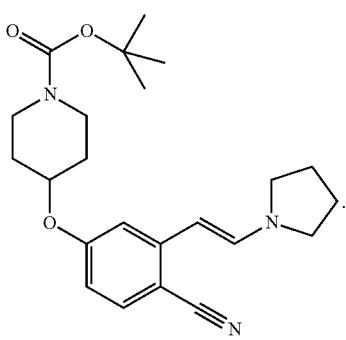

(VIb)

In a further embodiment of the present invention, in any of the compounds of formula (I), (III), (IV) or (VI) n is 2. In another embodiment of these compounds n is 3.

The oxygen (O) may be bound to the N-containing ring in any of the compounds of formula (I), (III), (IV) or (VI) in any position via a ring carbon atom. In one embodiment, n is 3 and O is attached to the 4-position of the resulting piperidine ring to give a compound of formula (Ic)

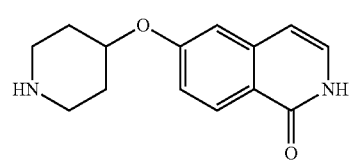

(Ic)

or, in another embodiment, the O is attached to the 3-position of the piperidine ring to give a compound of formula (Id)

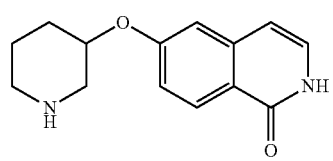

(Id)

in all their stereoisomeric forms.

In another embodiment, the O is attached to the 3-position of the pyrrolidine ring to give a compound of formula (Ie) in all their stereoisomeric forms.

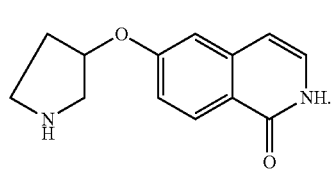

(Ie)

In addition, it is known in the art that the 2H-isoquinolin-1-ones of formula (I) shown in the schemes can also exist in their tautomeric form as 1-hydroxy-isochinolines and these tautomers are included in the scope of the present invention. Moreover, a compound of formula (I), (IV) or (VI) may contain a chiral carbon atom. Accordingly, these compounds exist in stereoisomeric forms, including enantiomers or diastereomers. These stereoisomeric forms and mixtures of stereoisomeric forms in all ratios are included in the scope of the present invention.

In one embodiment of the process of the present invention 6-(Piperidin-4-yloxy)-2H-isoquinolin-1-one or a salt thereof is prepared. In another embodiment, 6-(Piperidin-3-yloxy)-2H-isoquinolin-1-one or a salt thereof is prepared. In a further embodiment 6-(pyrrolidin-3-yloxy)-2H-isoquinolin-1-one or a salt thereof is prepared. In one embodiment the salt in any of these compounds is the hydrochloride salt.

The compound of formula (VI) may be used as intermediate in the preparation of Rho-kinase inhibitors. Thus, the present invention also relates to the use of a compound of formula (VI)

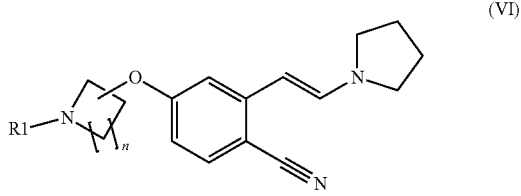

(VI)

wherein R1 is H or a protecting group, preferably R1 a protecting group, and
n is 1, 2, 3 or 4;
in the preparation of a compound of formula (I)

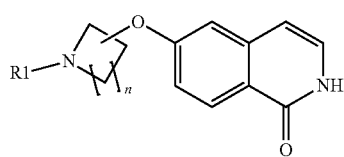

(I)

wherein
n is 1, 2, 3 or 4; and
R1 is H or a protecting group, preferably R1 is H.

EXAMPLES

In the following examples the processes and intermediates of the present invention are outlined in more detail. Accordingly, the following examples are part and embodiments of the present invention. They are also intended to illustrate but not to limit the present invention.

| Abbreviations | |
|---|---|
| rt | room temperature |
| DABCO | 1,4-Diazabicyclo[2.2.2]octane |
| DBU | 1,8-diazabicyclo[5.4.0]undec-7-ene |
| DMF | Dimethylformamide |
| DMFDMA | Dimethylformamide dimethylacetal |
| g | Gramm |
| ml | Milliliter |
| h | Hours |

EXAMPLES 1) 4-(4-Cyano-3-methyl-phenoxy)-piperidine-1-carboxylic acid tert-butyl ester (MW=316.40 g/mol)

a) 1.35 g 4-Fluoro-2-methyl-benzonitrile, dissolved in DMF, was added to 2.11 g 4-Hydroxy-piperidine-1-carboxylic acid tert-butyl ester and 0.6 g sodium hydride in 30 mL DMF. The mixture was stirred at room temperature (rt) until the reaction was complete. The reaction was quenched with water. The aqueous layer was extracted with ethylacetate (AcOEt) or methyl tert. butyl ether (MTB ether). The combined organic layers were washed with brine, dried and concentrated to give 2.6 g (yield 81%) 4-(4-Cyano-3-methyl-phenoxy)-piperidine-1-carboxylic acid tert-butyl ester. Mass: ($C_{18}H_{24}N_2O_3$): calcd. 316. found 261 [M+H−t($C_4H_9$)]$^+$ b) 22.6 g Potassium tert. butoxide, 33.2 g 4-Hydroxy-piperidine-1-carboxylic acid tert-butyl ester and 400 mL MTB ether were stirred for 1 h at reflux. A solution of 20.3 g 4-Fluoro-2-methyl-benzonitrile, dissolved in 250 mL MTB ether was added within 20 min to the suspension and heating to reflux was continued for 7 h. The reaction was quenched with water. The organic layer was separated and washed with water and concentrated to give 54.8 g (yield 92%) of 4-(4-Cyano-3-methyl-phenoxy)-piperidine-1-carboxylic acid tert-butyl ester. $^1$H NMR (500 MHz, $d_6$-DMSO) δ 1.40 (s, 9H), 1.47-1.55 (m, 2H), 1.88-1.95 (m, 2H), 2.43 (s, 3H), 3.13-3.22 (m, 2H), 3.63-3.70 (m, 2H), 4.66-4.73 (m, 1H), 6.96 (dd, J=8.6, 2.4 Hz, 1H), 7.07 (d, J=2.3 Hz, 1H), 7.67 (d, J=8.7 Hz, 1H).

2) 4-[4-Cyano-3-((E)-2-pyrrolidin-1-yl-vinyl)-phenoxy]-piperidine-1-carboxylic acid tert-butyl ester (MW=397.52 g/mol))

a) 47.3 g (0.15 mol) 4-(4-Cyano-3-methyl-phenoxy)-piperidine-1-carboxylic acid tert-butyl ester, 43.8 mL (0.33 mol) N,N-dimethylformamide dimethylacetal and 81.9 mL pyrrolidine (0.99 mol) were mixed and the mixture was heated within 30 min to 90° C. and kept at this temperature for 2 h. All volatile content was allowed to distil off. The temperature was raised to 120° C. and kept at this temperature for 27 h. Heating was discontinued and the dark highly viscous residue was dissolved in 400 mL MTB ether, washed twice with 200 mL saturated aqueous NaHCO$_3$ and once with 200 mL water. The organic layer was concentrated and recrystallised from isopropanol/water (245 mL/105 mL) collected and dried to yield 49.5 g (yield 83%, purity 96.4%) of 4-[4-Cyano-3-((E)-2-pyrrolidin-1-yl-vinyl)-phenoxy]-piperidine-1-carboxylic acid tert-butyl ester b) 94.6 g (0.3 mol) 4-(4-Cyano-3-methyl-phenoxy)-piperidine-1-carboxylic acid tert-butyl ester, 87.6 mL (0.66 mol) N,N-Dimethylformamide dimethylacetal, 109 mL (1.32 mol) pyrrolidine and 60.4 mL DMF (0.78 mol) were mixed and the mixture was heated within 30 min to 90° C. and kept at this temperature for 1 h. All volatile content was allowed to distil off. The temperature was raised to 110° C. and kept at this temperature for 2 h. The temperature was brought to 120° C. and kept at this temperature for 7.5 h. Heating was discontinued and the mixture was chilled to ambient temperature. Then, 200 mL water and 400 mL isopropanol were added. The mixture was stirred for 3 h at ambient temperature and 1 h at 5° C. to precipitate the product. The solid was collected rinsed with isopropanol/water (70/30) collected and dried to yield 113.7 g (yield 95.5%, purity 93.3%) of 4-[4-Cyano-3-((E)-2-pyrrolidin-1-yl-vinyl)-phenoxy]-piperidine-1-carboxylic acid tert-butyl ester c) 47.3 g (0.15 mol) 4-(4-Cyano-3-methyl-phenoxy)-piperidine-1-carboxylic acid tert-butyl ester, 43.8 mL (0.33 mol) N,N-Dimethylformamide dimethylacetal, 54.6 mL (0.66 mol) pyrrolidine and 30.2 mL DMF (0.39 mol) were mixed and the mixture was heated within 30 min to 90° C. and kept at this temperature for 1 h. All volatile content was allowed to distil off. The temperature was raised to 110° C. and kept at this temperature for 2.5 h. The temperature was brought to 120° C. and kept at this temperature for 5 h. Heating was discontinued and the mixture was chilled to ambient temperature, diluted with 400 mL MTB ether and washed twice with 200 mL saturated aqueous NaHCO$_3$ and once with 200 mL water. The organic layer was concentrated and recrystallized from isopropanol/water (245 mL/105 mL) collected and dried to yield 55.5 g (yield 93%, purity 100%) of 4-[4-Cyano-3-((E)-2-pyrrolidin-1-yl-vinyl)-phenoxy]-piperidine-1-carboxylic acid tert-butyl ester Off-white crystalline solid, melting point 115-117° C., $^1$H NMR (500 MHz, $d_6$-DMSO) δ 1.40 (s, 9H), 1.46-1.55 (m, 2H), 1.85-1.94 (m, 2H), 2.49-2.52 (m, 4H), 3.17-3.26 (m, 2H), 3.26-3.30 (m, 4H), 3.62-3.70 (m, 2H), 4.67-4.76 (m, 1H), 5.09 (d, J=13.6 Hz, 1H), 6.60 (dd, J=8.8, 2.4 Hz, 1H), 7.09 (d, J=2.4 Hz, 1H), 7.46 (d, J=8.9 Hz, 1H), 7.68 (d, J=13.7 Hz, 1H).

3) 6-(Piperidin-4-yloxy)-2H-isoquinolin-1-one hydrochloride (MW=280.80 g/mol)

42 g of 4-[4-Cyano-3-((E)-2-pyrrolidin-1-yl-vinyl)-phenoxy]-piperidine-1-carboxylic acid tert-butyl ester were added in portions to 135 mL of 1-butanol saturated with 48 g of HCL gas at 15° C. the mixture was heated to 63° C. within one h and stirred at 63-65° C. until completion of the reaction. The HCL containing solvent was exchanged by subsequent distillation and addition of fresh 1-butanol and the precipitate was collected, rinsed with 1-butanol and dried to yield 31.2 g (yield 106%, purity 96.5%) of 6-(Piperidin-4-yloxy)-2H-isoquinolin-1-one hydrochloride.

$^1$H NMR (500 MHz, $d_6$-DMSO) δ 1.85-1.95 (m, 2H), 2.13-2.22 (m, 2H), 3.04-3.14 (m, 2H), 3.20-3.29 (m, 2H), 4.79-4.86 (m, 1H), 6.44 (d, J=7.1 Hz, 1H), 7.10 (dd, J=8.9, 2.5 Hz, 1H), 7.14 (dd, J=7.2, 6.7 Hz, 1H), 7.22 (d, J=2.5 Hz, 1H), 8.09 (d, J=8.6 Hz, 1H), 8.97-9.13 (bs, 2H) 11.09 (bd, J=5 Hz, 1H).

The invention claimed is:

1. A process for the preparation of a compound of the formula

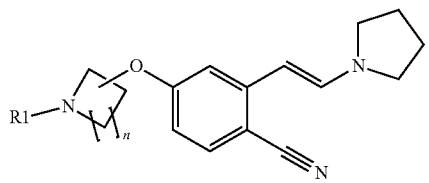

(VI)

wherein
n is 1, 2, 3 or 4; and
R1 is H or a protecting group,
comprising
(B) reacting a compound of formula (IV)

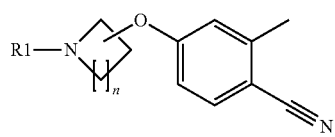

(IV)

wherein R1 is a protecting group
with a mixture of a reagent of the formula (R2O)$_2$HC—N(CH$_3$)$_2$ (V), wherein R$_2$ is (C$_1$-C$_6$)alkyl, and pyrrolidine, wherein reagent (V) is used in a molar excess of 1.5 or more equivalents and the pyrrolidine is used in a molar excess of 4.0 or more equivalents over a compound of formula (IV); and
optionally removing the protection group in a compound of formula (VI) to give a compound of formula ((VI) wherein R1 is H.

2. The process according to claim 1, wherein 2.0 to 7.0 equivalents of reagent (V) relative to a compound of formula (IV) are used.

3. The process according to claim 1, wherein the reagent (V) is N,N Dimethylformamid-dimethylacetal.

4. The process according to claim 1, wherein 4.0 to 9.0 equivalents pyrrolidine relative to a compound of formula (IV) are used.

5. The process according to claim 1, wherein DMF is added.

6. A process for the preparation of a compound of formula (I)

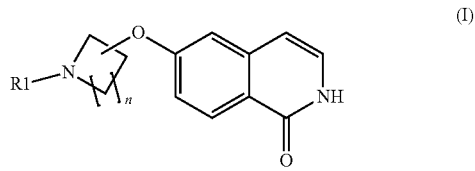

(I)

or a salt thereof, wherein
n is 1, 2, 3 or 4; and
R1 is H or a protecting group,
comprising the steps of
(B) preparing a compound of formula (VI)

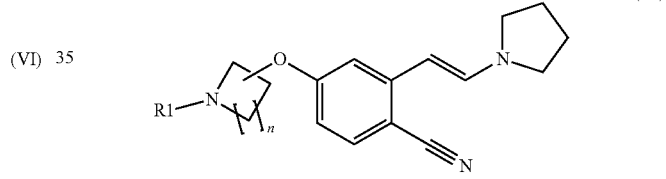

(VI)

wherein R1 is a protecting group and
n is 1, 2, 3 or 4;
according to claim 1,
(C) cyclising a compound of formula (VI) in the presence of a hydrohalic acid in a suitable solvent and whereby the protecting group is optionally removed
to give a compound of formula (I), wherein R1 is H or a protecting group;
(D) optionally removing the protecting group from a compound of formula (I), if R1 is a protecting group, to give compound a formula (I) wherein R1 is H, and
(E) optionally converting a compound of formula (I) into a salt thereof.

7. The process according to claim 6, wherein the hydrohalic acid used in the cyclisation step is HCl.

8. The process according to claim 1, wherein n is 2 or 3.

9. The process according to claim 1, wherein the protecting group is acid-labile.

10. The process according to claim 1, wherein the protecting group in R1 is tert-butoxycarbonyl.

11. The process according to claim 1, wherein the compound of formula (IV) is prepared by reacting a compound of formula (II)

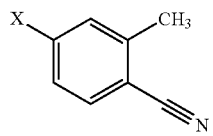

(II)

wherein X is halogen,
in a suitable solvent and in the presence of a base selected from an alkali metal alkoxide, alkali metal hydride or alkali metal with a compound of formula (III)

(III)

wherein
R1 is H or a protecting group and
n is 1, 2, 3 or 4,
and, if R1 is H, the amino group in a compound of formula (IV) is protected to give a compound of formula (IV), wherein R1 is a protecting group.

12. A compound of formula (VI)

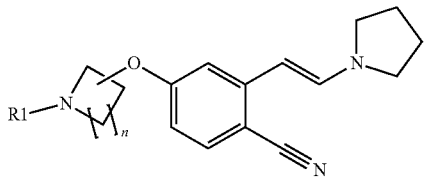

(VI)

wherein R1 is H or a protecting group and
n is 1, 2, 3 or 4.

13. The compound according to claim 12, wherein the protecting group is an acid-labile protecting group.

14. The compound according to claim 13, wherein the acid-labile protecting group is tert-butyloxycarbonyl.

15. The compound according to claim 12, wherein n is 2 or 3.

16. The compound according to claim 12, which is 4-[4-Cyano-3-((E)-2-pyrrolidin-1-yl-vinyl)-phenoxy]-piperidine-1-carboxylic acid tert-butyl ester.

* * * * *